(12) United States Patent
Dinkler

(10) Patent No.: US 6,306,146 B1
(45) Date of Patent: Oct. 23, 2001

(54) SURGICAL INSTRUMENT SUPPORT AND METHOD

(75) Inventor: Charles E. Dinkler, Cincinnati, OH (US)

(73) Assignee: Ohio Medical Instrument Company, Inc., Cincinnati, OH (US)

( * ) Notice: Subject to any disclaimer, the term of this patent is extended or adjusted under 35 U.S.C. 154(b) by 0 days.

(21) Appl. No.: 09/543,875

(22) Filed: Apr. 6, 2000

(51) Int. Cl.$^7$ .................................................. A61B 19/00
(52) U.S. Cl. .......................... 606/130; 600/417; 600/429
(58) Field of Search ................................ 606/130, 1, 108, 606/56; 600/229, 233, 407, 427, 429, 426, 417, 411, 414

(56) References Cited

U.S. PATENT DOCUMENTS

| | | |
|---|---|---|
| 4,805,615 | 2/1989 | Carol . |
| 4,955,891 | 9/1990 | Carol . |
| 5,116,345 | 5/1992 | Jewell et al. . |
| 5,529,358 | 6/1996 | Dinkler et al. . |
| 5,695,501 | 12/1997 | Carol et al. . |
| 5,810,712 | 9/1998 | Dunn . |
| 5,891,157 | 4/1999 | Day et al. . |
| 5,891,158 | 4/1999 | Manwaring et al. . |
| 5,961,456 | 10/1999 | Gildenberg . |
| 5,971,997 | 10/1999 | Guthrie et al. . |
| 5,984,930 | 11/1999 | Maciunas et al. . |
| 6,110,182 * | 8/2000 | Mowlai-Ashtiani ................. 606/130 |
| 6,117,143 * | 9/2000 | Hynes et al. .......................... 606/130 |

OTHER PUBLICATIONS

OMI Surgical Products, Mayfield/ACCISS: An Interactive, Image–Guided Stereotactic Planing and Navigation System, Brochure (1996).

Dorward et al., Clinical Introduction of an Adjustable Rigid Instrument Holder for Frameless Stereotactic Interventions, Computer Aided Surgery, 2:180–185 (1997).

Philips, Frameless Sterotactic Biopsy with the EasyGuide, Medicamundi, pp. 33–37; vol. 42, Issue 1, Mar., 1998.

Patel et al., A Simple Trajectory Guidance Device that Assists Freehand and Interactive Image Guided Biopsy of SMall Deep Intracranial Targets, Computer Aided Surgery, 2:186–192 (1997).

* cited by examiner

Primary Examiner—Pedro Philogene
(74) Attorney, Agent, or Firm—Wood, Herron & Evans, L.L.P.

(57) ABSTRACT

A surgical instrument support is provided having an articulated arm with first structure on a proximal end of the arm. A lockable target ball is rotatably mounted on a distal end of the articulated arm, and the lockable ball has a diametric hole therein for receiving and supporting a surgical instrument. A mount has second structure that receives and secures the proximal end of the articulated arm. The first structure on the articulated arm cooperates with the second structure on the mount to automatically align the proximal end of the articulated arm with the mount in a repeatable relationship. The mount is adapted to be releasably attached to a fixed structure. Thus, after establishing a desired alignment of the lockable ball to a patient, the articulated arm can be removed from the fixed structure and then subsequently remounted therein without losing the desired alignment of the lockable ball with the patient.

30 Claims, 4 Drawing Sheets

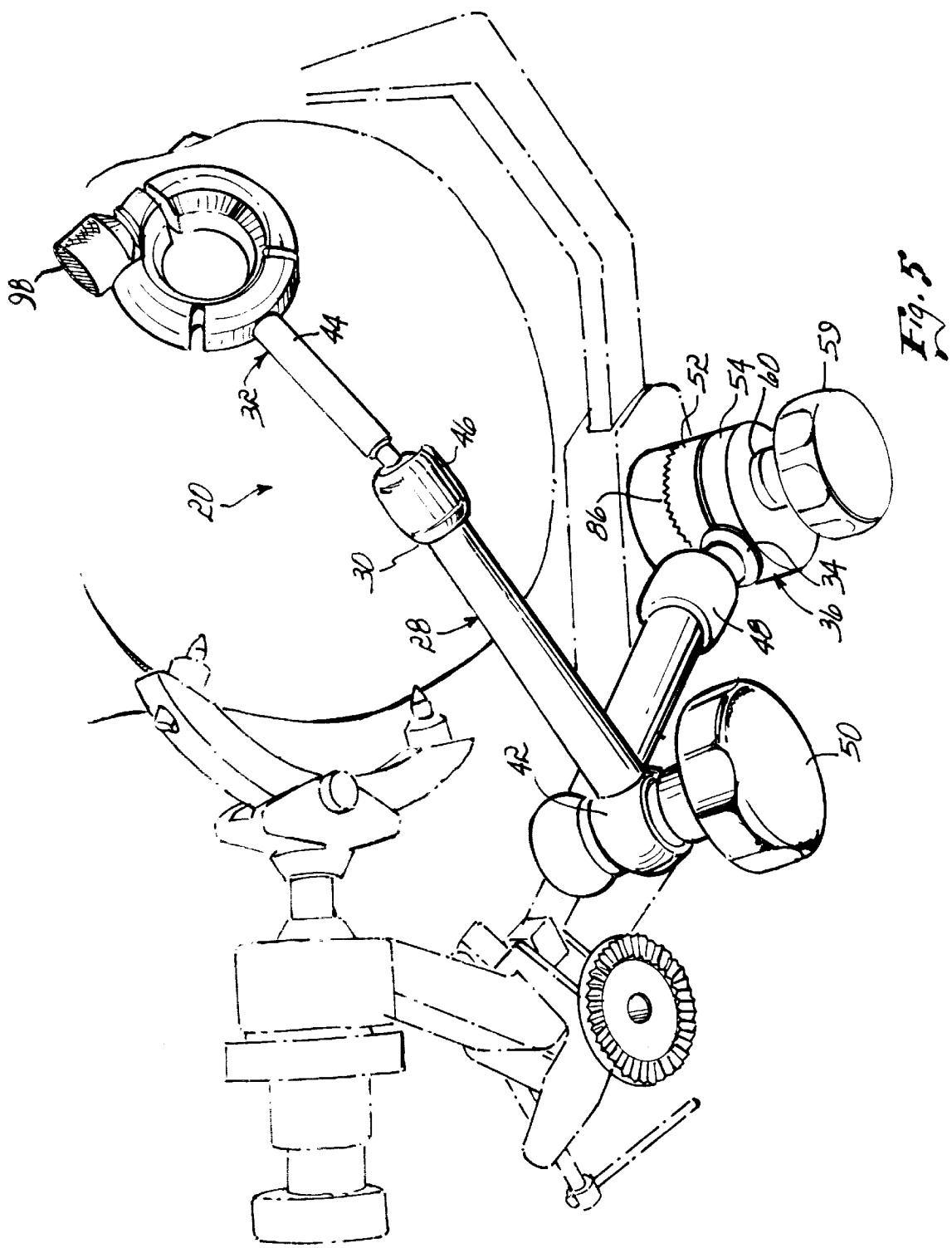

SURGICAL INSTRUMENT SUPPORT AND METHOD

FIELD OF THE INVENTION

This invention relates to neurosurgical apparatus generally, and more particularly, to an improved surgical instrument support.

BACKGROUND OF THE INVENTION

It is known to define and correlate the position of single or multiple points within the cranium with preoperative imaging by using frameless stereotactic systems such as the MAYFIELD/ACCISS Stereotactic Workstation which is commercially available from the assignee of this application. Frameless systems provide constant intraoperative navigational information, which permits a surgeon to identify precisely the spacial position of a probe in the surgical field with CT or MRI scan data shown on a high definition display monitor.

With a frameless stereotactic system, an intracranial target point is accessed by advancing a probe along a predetermined linear path or trajectory to the target point within the patient's skull. To provide the necessary stabilization of tooling during its advance along the linear trajectory, a surgical instrument support is used. The surgical instrument support is comprised of an articulated arm having a proximal end mounted on a patient support or other fixed structure and a lockable tool socket rotatably mounted on a distal end of the arm. The surgical instrument support allows a surgical instrument to be moved to the intracranial target point along a stable and fixed linear trajectory. By fixing the trajectory on the intracranial target point, the risk of misdirection or drift associated with freehand procedures is eliminated.

One example of a known surgical instrument support is the "EASYGUIDE" navigator system commercially available from Phillips Medical Systems N.A. Inc. of Shelton, Connecticut. Another example of a surgical instrument support is commercially available from the assignee of the present invention. Other examples of known surgical instrument supports are shown in U.S. Pat. Nos. 5,695,501 and 5,810,712, which are assigned to the assignee of this invention and hereby expressly incorporated by reference herein. All of these devices include a lockable ball rotatably mounted in a tool holder on the end of an articulated arm as described above. The ball has a diametric hole that receives an instrument. In a known manner, a known locating probe is inserted into the ball with the tip of the probe normally being positioned substantially at the center of the ball. The probe presents a linear image on a display monitor that is also displaying CT or MRI scan data of the patient. Thus, as the probe is moved, a path between the tip of the probe and a selected target point displayed with the scan data can be tracked. By moving the distal end of the articulated arm, the probe and ball are first located at a desired position with respect to the skull that defines a desired trajectory between the tip of the probe and the target point. The articulated arm is then locked, thereby locking the ball at the desired position. Next, the probe and ball are rotated to align a centerline of the hole in the ball with the desired trajectory, so that an instrument inserted through the hole in the ball follows the desired trajectory and intersects the target point. The ball is then locked in place, so that it cannot rotate with respect to the tool holder on the distal end of the articulated arm; and hence the orientation of the probe or other tool within the ball is fixed with respect to the target point. With the ball thus aligned, the probe is removed and other surgical instruments inserted into the ball are automatically aligned with the intracranial target point.

While these prior art devices have proved suitable for their intended purposes, they all have one particular disadvantage. In the above described process, after the surgeon has established the desired trajectory by locking the articulated arm and ball in place, the articulated arm and ball can interfere with procedures that are being conducted within the surgical field that do not require the presence of the articulated arm and ball. Thus, it is often desirable and sometimes necessary to move the articulated arm and ball from the surgical field. With known devices, any attempt to move the articulated arm and ball results in a loss of the desired trajectory that had been previously determined, thus requiring that the surgeon repeat the alignment process by which the desired trajectory was originally determined.

Therefore, there is a need for an improved surgical instrument support that can be moved from the surgical field and subsequently returned to its initial position without losing a previously established desired trajectory with respect to an intracranial target point.

SUMMARY OF INVENTION

The present invention provides an improved surgical instrument support that offers more flexibility than known instrument holders. The surgical instrument support of the present invention permits difficult surgical procedures to be performed in less time and with less stress, that is, more efficiently, and without any loss in accuracy or precision. The surgical instrument support of the present invention has the advantage of being able to automatically re-establish a desired alignment of the instrument support after it has been removed from its fixed mount. The invention is especially useful in those situations where after aligning the instrument support with a patient, it is necessary to perform procedures in the surgical field that do not require the surgical instrument support. With the surgical instrument support of the present invention, once its desired position and orientation are precisely aligned with the patient, it can be removed from the surgical field and then, upon being placed back into its mount, the desired position and orientation are automatically re-established without repeating the original alignment process.

In accordance with the principles of the present invention and the described embodiments, a surgical instrument support is provided having an articulated arm with a first structure on a proximal end of the arm. A lockable target ball is rotatably mounted on a distal end of the articulated arm. The lockable ball has a diametric hole therein for receiving and supporting a surgical instrument. A mount has a second structure that receives and secures the proximal end of the articulated arm. The first structure on the articulated arm cooperates with the second structure on the mount to automatically align the proximal end of the articulated arm with the mount in a repeatable relationship. The mount is adapted to be releasably attached to a fixed structure.

In one aspect of the invention, the proximal end of the articulated arm has a cross-sectional profile, and the mount has a hole with a cross-sectional profile that receives the proximal end of the articulated arm in a repeatable relationship. The mount further has a clamp for securing the proximal end of the articulated arm in the hole in the mount. In a further aspect of the invention, the cross-sectional profiles of the first and second structures are noncircular profiles. Thus, the surgical instrument support of the present invention permits removal and remounting of the articulated arm without losing the desired position and orientation of the lockable target ball with respect to a patient.

In another embodiment, the present invention includes a method of performing a surgical procedure that includes first moving a distal end of an articulated arm having a target ball rotatably mounted therein to a desired position. The joints of the articulated arm are locked to maintain the target ball at the desired position. Next, the target ball is rotated to a desired orientation, and the target ball is locked at the desired orientation. The proximal end of the articulated arm is then unclamped from a mount attached to a fixed structure. The proximal end of the articulated arm has a desired relationship with respect to the mount, and the proximal end of the articulated arm is removed from the mount. The articulated arm is then inserted into the mount such that first structure on the articulated arm cooperates with second structure on the mount to automatically align the proximal end of the articulated arm with the mount in the desired relationship. Thus, the target ball is automatically placed at the desired position and the desired orientation.

Various additional advantages, objects and features of the invention will become more readily apparent to those of ordinary skill in the art upon consideration of the following detailed description of the presently described embodiments taken in conjunction with the accompanying drawings.

BRIEF DESCRIPTION OF DRAWINGS

FIG. 5 is a perspective view of the invention in a second application in accordance with the principles of the present invention.

DETAILED DESCRIPTION OF THE INVENTION

Figure 1:
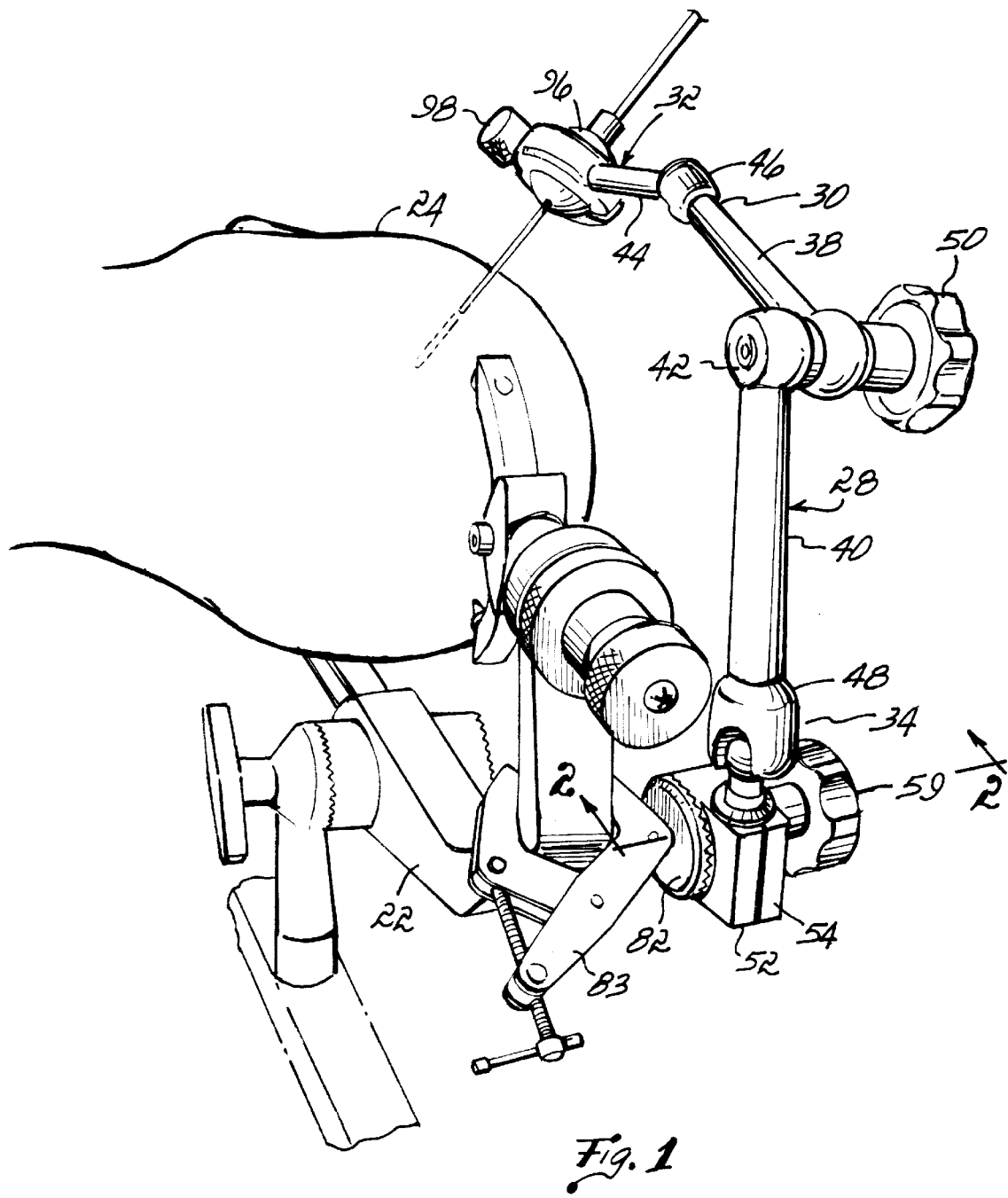
FIG. 1 is a perspective view of a surgical instrument support in a first application in accordance with the principles of the present invention.

Referring to FIG. 1, a surgical instrument support 20 is mounted on a surgical skull clamp 22 that is supporting the head 24 of a patient. The skull clamp 22 is mounted at the end of a patient support, for example, an operating table, (not shown) in a known manner. The surgical tool support 20 includes an articulated arm 28 having a distal end 30 connected to a tool holder 32 and a proximal end 34 connected to a mount 36. The articulated arm 28 is comprised of two links 38, 40 that have ends rotatably connected together to form a pivot joint 42. An opposite end of the link 38 is connected to an end of a shaft 44 of the tool holder 32 via a ball and socket joint 46 such that the end of the shaft 44 can rotationally swivel with respect to the end of the shaft 38. Similarly, the opposite end of the second link 40 is connected by a ball and socket joint 48 to the proximal end 34, thereby permitting the articulated arm 28 to rotationally swivel with respect to the proximal end 34. The pivot joint 42 and swivel joints 46, 48 are clamped and unclamped by rotating a knob 50. The assembly of the pivoting links 38, 40 with the swivel joints 46, 48 is commercially available as a tool holder from J&L Industrial Supply of Plainview, N.Y. The tool holder 32 with shaft 44 is commercially available as an "ACCUPOINT" tool holder from Ohio Medical Instrument Company of Cincinnati, Ohio. For this invention, the end of the shaft 44 of the ACCUPOINT tool holder has been fitted with a ball (not shown) which is assembled into the swivel joint 46 in a known manner; and the proximal end 34 has a ball (not shown) which is assembled into the swivel joint 48 in a known manner.

Figure 2:
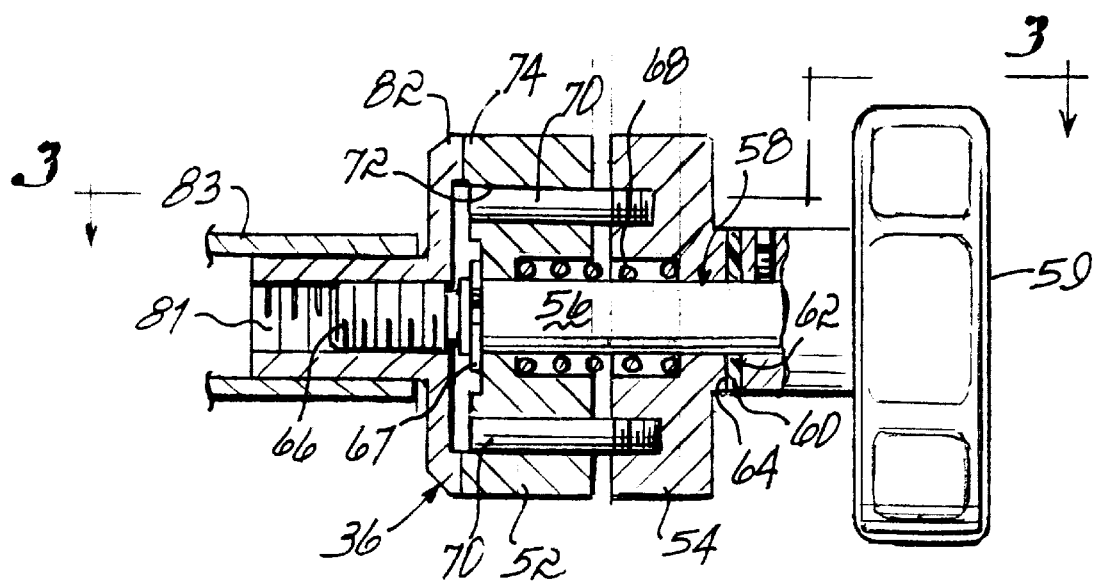
FIG. 2 is a partial cross-sectional view of the mount taken generally along the line 2—2 of FIG. 1.
Figure 3:
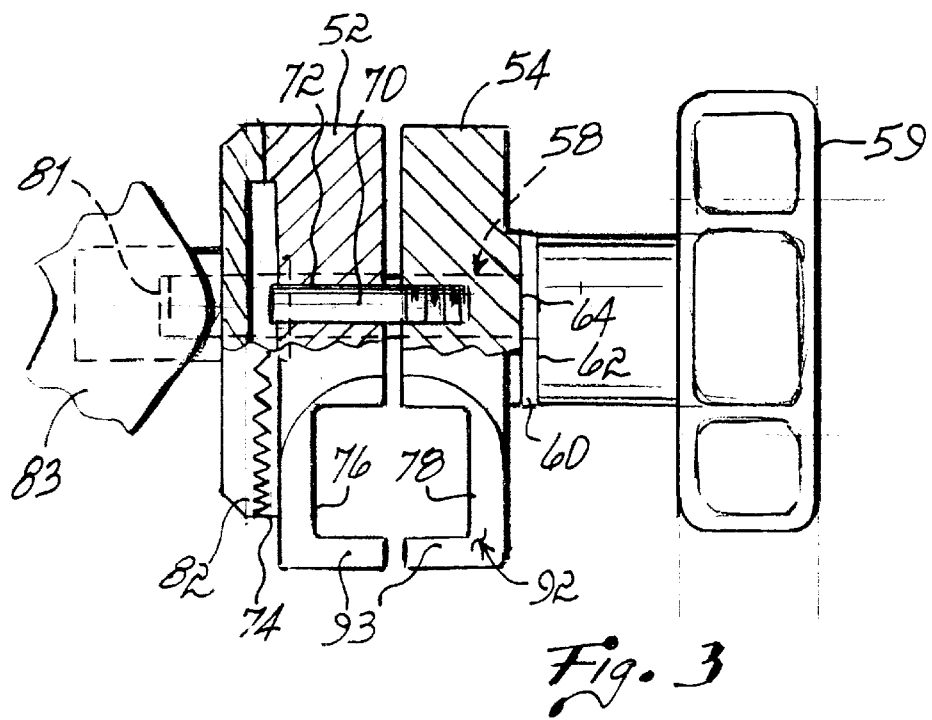
FIG. 3 is a partial cross-sectional view of the mount taken generally along the line 3—3 of FIG. 2.

Referring to FIG. 2, the mount 36 includes first and second blocks 52, 54 slidably mounted on a relieved or smooth portion 56 of a shaft 58. A knob 59 is rigidly connected to one end of a shaft 58, and a bearing washer 60 is located on the shaft 58 between the lower surface 62 of the knob 59 and an outer surface 64 of the block 54. The block 52 is prevented from moving over the threaded portion 66 of the shaft 58 by a lock ring 67 mounted on the shaft 58 in a known manner. The smooth portion 56 of the shaft 58 has a length permitting the blocks 52, 54 to slide axially with respect to each other. A biasing element 68, for example, a compression spring, is mounted over the shaft 58 between the blocks 52, 54 and biases the blocks away from each other such that a small gap is formed therebetween, for example, of approximately 0.100 inches. At least one guide pin 70 (FIG. 3) is pressed into one of the sliding blocks, for example, the block 54, and slidingly engages a bore 72 in the other block 52. The guide pin 70 and bore 72 function to prevent the blocks 52, 54 from rotating with respect to each other on the shaft 58. Normally, a pair of guide pins 70 and bores 72 are used. The block 52 has a known annular toothed or starburst connector 74 on its outer end. Such a starburst connector is normally a circular structure in which the connector portion is an annular ring of adjacent, radially extending serrations or teeth.

Upon rotating the knob 59, for example, clockwise, the threaded portion 66 of the shaft 58 is threaded into a center hole 81 of a starburst connector 82 mounted on a Kant Twist clamp 83. The starburst connector 74 is brought into mating contact with the starburst connector 80, thereby securing the mount 36 to the Kant Twist clamp 83. The blocks 52, 54 have respective first and second structures 76, 78, for example, opposed U-shaped channels, that together form a hole having a substantially square, cross-sectional profile or shape. The cross-sectional profile of the structures 76, 78 match and receive the structure 80 (FIG. 4) on the proximal end 34 of the articulated arm 28. The structure 80 has a substantially square, cross-sectional profile or shape that slides into the combined structures 76, 78. Further rotation of the knob 59 moves the block 54 toward the block 52, thereby clamping the proximal end 34 of the articulated arm 28 between the blocks 52, 54. As the knob 59 is rotated in an opposite direction, for example, counterclockwise, the block 54 is separated from the block 52 by the compression spring 68, thereby releasing the proximal end 34 of the articulated arm 20 prior to the starburst connectors 74, 80 separating. Thus, the structure of the mount 36 permits the articulated arm 28 to be removed from the mount 36 without disturbing the mechanical connection of the mount 36 to a fixed element, for example, the Kant Twist clamp 83.

In use, the mount 36 can be attached to a Kant Twist clamp 84 as illustrated in FIG. 1 or, alternatively, connected to a starburst connector 86 (FIG. 5) on the base of the skull clamp 22. Next, rotating the knob 59, the threaded portion of the shaft 58 is threaded into a center hole (not shown) of one of the starburst connectors 82, 86 in a known manner. The knob 59 is rotated until the starburst connector 74 on the mount 36 is engaged with its mating starburst connector 82, 86 in the desired manner. This is achieved by rotating the knob 50 until the starburst connectors are brought together. At this point, the compression spring 68 continues to hold the blocks 52, 54 apart, thereby facilitating the insertion of the square shaft 80 (FIG. 4) of the distal end 34 of the articulated arm 28 into the hole formed by the structure 76, 78 of the blocks 52, 54.

Figure 4:
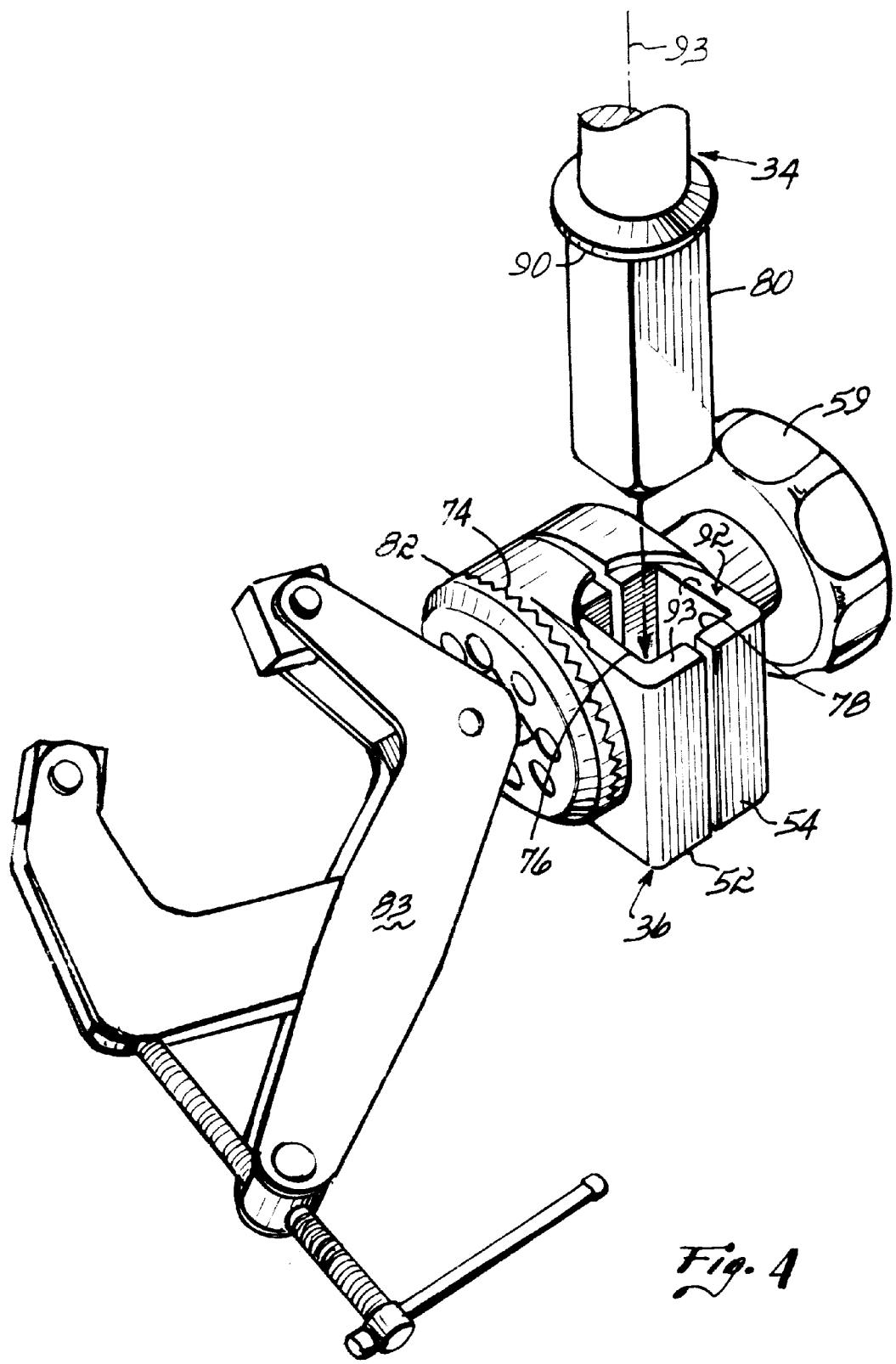
FIG. 4 is a partial perspective view illustrating the coupling between the proximal end of the articulated arm and the mount of FIG. 1.

The distal end 34 of the articulated arm 28 is properly seated in the mount 36 when a locating surface 90 (FIG. 4)

on the proximal end 34 of the articulated arm 28 contacts a stop surface 92 on the mount 36. The locating surface 90 is a generally annular surface surrounding the structure 80 and is located in a plane substantially perpendicular to a longitudinal centerline 93 of the structure 80. Similarly, two substantially coplanar and flat surfaces 93 on each of the blocks 52, 54 form the generally annular stop surface 92 that surrounds the structure 76, 78 of the respective blocks 52, 54. With the proximal end 34 of the articulated arm 28 properly seated in the mount 36, the knob 50 is again rotated to move the blocks 52, 54 together, thereby clamping the proximal end 34 of the articulated arm 28 to the mount 36.

Thereafter, in a known manner, referring to FIG. 1, the articulated arm is manipulated to bring the tool holder 32 to a desired position with respect to the head 24. The locking knob 50 is rotated to lock the pivot joint 42 and swivel joints 46, 48, thereby locking the tool holder 32 in its desired position. The target ball 96 is then rotated until the desired trajectory with the intracranial target point is achieved, and the target ball is locked at its desired orientation by rotating the locking knob 98.

The surgical instrument support 20 is now at its desired position to perform a surgical procedure. However, prior to the procedure, or as a part of the procedure, it may be necessary to perform other procedures in the surgical field that do not require the presence of the surgical instrument support 20. The surgical instrument support 20 often interferes with the performance of such procedures, and it is desirable and sometimes necessary to move the surgical instrument support 20 from its previously aligned position. With known systems, any attempt to move or remove the surgical instrument support 20 from the aligned position results in a loss of that alignment. However, with the present surgical instrument support, the clamping knob 59 is rotated in a direction to loosen or separate the blocks 52, 54. As the knob 59 is rotated, for example, one revolution, the biasing element 68 separates the block 54 from the block 52 without permitting the starburst connector 74 to separate from a mating connector 82, 86. Thus, the distal end 34 of the articulated arm is released from the mount 36 while the mount 36 remains connected to a fixed element.

The distal arm can then be removed from the clamp 36 for any desired period. When the distal arm 28 is again required, the structure 80 having the substantially square, cross-sectional profile is inserted into the structure 76, 78 forming the generally substantially square hole (FIG. 4). The substantially square, cross-sectional profiles of the structures 76, 78, 80 cause the proximal end 34 of the articulated arm 28 to automatically align with the mount 36 in a desired relationship that existed when the articulated arm 28 was removed from the clamp 36. Further, the seating of the locating surface 90 onto the stop surface 92 further guarantees that the articulated arm 28 is exactly in the same relationship that it had with respect to the mount 36 before the articulated arm 28 was removed therefrom. The knob 59 is again tightened, thereby moving the block 54 toward the block 52 and clamping the distal end 34 of the articulated arm 28 in the mount 36. As will be appreciated, such a capability would not be possible if the structure 80 and mating on the distal end 34 of the articulated arm 28 and the mating structure 76, 78 had only a circular, cross-sectional profile.

Thus, the present invention provides an improved surgical instrument support that offers more flexibility than known instrument holders. The surgical instrument support of the present invention permits difficult surgical procedures to be performed in less time and with less stress, that is, more efficiently, and without any loss in accuracy or precision. The invention is especially useful in those situations where after aligning the instrument support with a patient, it is necessary to perform procedures in the surgical field that do not require the surgical instrument support. With the surgical instrument support of the present invention, once it's desired position and orientation are precisely aligned with the patient, it can be removed from the surgical field and then, upon being placed back into its mount, the desired position and orientation are automatically re-established without repeating the original alignment process.

While the present invention has been illustrated by a description of various described embodiments and while these embodiments have been described in considerable detail in order to describe the best mode of practicing the invention, it is not the intention of Applicant to restrict or in any way limit the scope of the appended claims to such detail. Additional advantages and modifications within the spirit and scope of the invention will readily appear to those skilled in the art. For example, in the described embodiment, the structure 76, 78 of the mount 36 and the mating structure 80 on the proximal end 34 of the articulated arm 28 have substantially square, cross-sectional profiles. As will be appreciated, the invention is effective if those components have structure with any cross-sectional profile that causes the proximal end of the articulated arm to automatically align in the desired relationship with the mount 36. For example, other multi-lateral, cross-sectional profiles such as triangular, hexagonal, octagonal, etc., cross-sectional profiles are effective. Further, arcuate cross-sectional profiles that include a circular shaft with a key, spline or other angular positioning feature, may also be used. In addition, the cross-sectional profiles may be non-circular, for example, elliptical in nature. The features 76, 78 of the clamp 36, 80 of the distal end 34 of the articulated arm 28 may also taper axially.

As will be appreciated, it is also not necessary that the cross-sectional profiles of the feature 80 on the proximal end 34 of the articulated arm 28 be identical to the cross-sectional profile of the features 76, 78 of the mount 36. For example, the cross-sectional profile of the feature 80 may be elliptical; and the cross-sectional profile of the features 76, 78 of the mount 36 may be multi-lateral, for example, rectangular. In the described embodiment, the features 76, 78 of the blocks 52, 54 fully surround the feature 80 on the distal end 34 of the articulated arm 28. As will be appreciated, the features 76, 78 do not have to fully surround the feature 80 but merely contact the feature 80 sufficiently to provide the desired alignment and clamping features.

Therefore, the invention in its broadest aspects is not limited to the specific detail shown and described. Consequently, departures may be made from the details described herein without departing from the spirit and scope of the claims which follow.

What is claimed is:

1. A surgical instrument support comprising:
    an articulated arm having distal and proximal ends, the proximal end having first structure;
    a lockable target ball rotatably mounted on the distal end of the articulated arm, the lockable ball having a diametric hole therein adapted to receive a surgical instrument; and
    a mount having second structure and receiving and securing the proximal end of the articulated arm, first structure on the articulated arm cooperating with the second structure on the mount to automatically align the proximal end of the articulated arm with the mount in a repeatable relationship, the mount adapted to be releasably attached to a fixed structure.

2. The surgical instrument support of claim 1 wherein the first structure on the articulated arm has a cross-sectional profile and the second structure on the mount has a cross-sectional profile for repeatedly receiving and holding the proximal end of the articulated arm in a desired relationship.

3. The surgical instrument support of claim 2 wherein the first structure on the proximal end of the articulated arm has a noncircular cross-sectional profile.

4. The surgical instrument support of claim 3 wherein the second structure on the mount further comprises an opening having a noncircular cross-sectional profile for repeatedly receiving the proximal end of the articulated arm in the desired relationship.

5. The surgical instrument support of claim 4 wherein the mount further comprises a clamp for securing the proximal end of the articulated arm in the opening in the mount.

6. The surgical instrument support of claim 5 wherein the mount further comprises a connector adapted to attach the mount to the fixed structure.

7. The surgical instrument support of claim 5 wherein the proximal end of the articulated arm has a locating surface in a plane substantially perpendicular to a centerline of the proximal end of the articulated arm.

8. The surgical instrument support of claim 7 wherein the locating surface is a substantially annular surface.

9. The surgical instrument support of claim 7 wherein the mount further has a stop surface contacting the locating surface upon the proximal end of the articulated arm being inserted into the opening in the mount.

10. The surgical instrument support of claim 9 wherein the stop surface is comprised of two substantially coplanar surfaces forming a substantially annular surface around the opening in the mount.

11. The surgical instrument support of claim 1 wherein the mount further comprises:
a first block;
a second block, the first and second blocks receiving the proximal end of the articulated arm in an automatically repeatable relationship with respect to the mount; and
a clamp for securing the first and second blocks and the proximal end of the articulated arm together.

12. The surgical instrument support of claim 11 wherein the proximal end of the articulated arm has a first noncircular cross-sectional profile and each of the first and second blocks have openings with second noncircular cross-sectional profiles such that the proximal end of the articulated arm is receivable by the openings in the first and second blocks in a manner automatically aligning the proximal end of the articulated arm with the openings in the first and second blocks in a repeatable relationship.

13. The surgical instrument support of claim 12 wherein the first and second noncircular cross-sectional profiles are multilateral profiles.

14. The surgical instrument support of claim 13 wherein the multilateral profiles are square profiles.

15. The surgical instrument support of claim 11 wherein the mount further comprises a threaded shaft adapted to threadedly engage the fixed structure.

16. The surgical instrument support of claim 15 further comprising a manually operable knob connected to one end of the threaded shaft.

17. The surgical instrument support of claim 15 wherein the threaded shaft extends through the first and second blocks to clamp the first and second blocks to the proximal end of the articulated arm as the threaded shaft is threadedly engaged with the fixed structure.

18. The surgical instrument support of claim 17 further comprising a biasing element for applying a biasing force on the first and second blocks tending to separate the first and second blocks.

19. The surgical instrument support of claim 18 wherein the biasing element is a compression spring.

20. The surgical instrument support of claim 19 wherein the compression spring is mounted on the threaded shaft between the first and second blocks.

21. The surgical instrument support of claim 18 wherein one of the first and second blocks has a guide rod rigidly connected thereto and the other of the first and second blocks has a hole receiving the guide rod to prevent the first and second blocks from rotating with respect to each other.

22. An apparatus comprising:
a surgical skull clamp;
an articulated arm having distal and proximal ends, the proximal end having first structure;
a lockable target ball rotatably mounted on the distal end of the articulated arm, the lockable ball having a diametric hole therein adapted to receive a surgical instrument; and
a mount having second structure and receiving and securing the proximal end of the articulated arm, first structure on the articulated arm cooperating with the second structure on the mount to automatically align the proximal end of the articulated arm with the mount in a repeatable relationship, the mount being releasably attachable to the surgical skull clamp.

23. The apparatus of claim 22 wherein the mount further comprising a threaded shaft threadedly engaging the surgical skull clamp for releasably attaching the mount to the surgical skull clamp.

24. The apparatus of claim 23 wherein the mount has a first mounting surface and the surgical skull clamp has a second mounting surface contacting the first mounting surface upon the mount being releasably attached to the surgical skull clamp.

25. The apparatus of claim 24 wherein the first and second mounting surfaces are mating toothed surfaces.

26. The apparatus of claim 22 further comprising a Kant Twist clamp releasably attachable to the mount and the surgical skull clamp.

27. The apparatus of claim 26 wherein the mount further comprising a threaded shaft threadedly engaging the Kant Twist clamp for releasably attaching the mount to the Kant Twist clamp.

28. The apparatus of claim 27 wherein the mount has a first mounting surface and the Kant Twist clamp has a second mounting surface contacting the first mounting surface upon the mount being releasably attached to the Kant Twist clamp.

29. The apparatus of claim 28 wherein the first and second mounting surfaces are mating toothed surfaces.

30. A method of performing a surgical procedure comprising:
moving a distal end of an articulated arm having a target ball rotatably mounted therein to a desired position;
locking the joints of the articulated arm to maintain the target ball at the desired position;
rotating the target ball to a desired orientation;
locking the target ball at the desired orientation;
unclamping a proximal end of the articulated arm from a mount attached to a fixed structure, the proximal end of the articulated arm having a desired relationship with respect to the mount;
removing the proximal end of the articulated arm from the mount;
remounting the articulated arm in the mount such that first structure on the articulated arm cooperates with second structure on the mount to automatically align the proximal end of the articulated arm with the mount in the desired relationship, thereby automatically placing the target ball at the desired position and the desired orientation.

* * * * *